United States Patent [19]

Freidinger et al.

[11] 4,360,516
[45] * Nov. 23, 1982

[54] MODIFIED D-RETRO CYCLIC HEXAPEPTIDE SOMATOSTATIN ANALOGS

[75] Inventors: Roger M. Freidinger, Hatfield; Daniel F. Veber, Ambler, both of Pa.

[73] Assignee: Merck & Co., Inc., Rahway, N.J.

[*] Notice: The portion of the term of this patent subsequent to Jan. 12, 1998, has been disclaimed.

[21] Appl. No.: 254,010

[22] Filed: Apr. 13, 1981

[51] Int. Cl.³ .................. A61K 37/00; C07C 103/52
[52] U.S. Cl. .............................. 424/177; 260/112.5 S
[58] Field of Search ................. 260/112.5 S; 424/177

[56] References Cited

U.S. PATENT DOCUMENTS 4,108,987  8/1978  Veber et al. ................. 260/112.5 R
4,235,886  11/1980  Freidinger et al. ................. 424/177

OTHER PUBLICATIONS

Journal of the American Chemical Society, 101, pp. 6129–6131, (1979); Freidinger et al. (II).
Accounts of Chemical Research 12, pp. 1–7, (1979), Goodman et al.

Primary Examiner—Delbert R. Phillips
Attorney, Agent, or Firm—David L. Rose; Mario A. Monaco

[57] ABSTRACT

Highly active and long lasting cyclic hexapeptide analogs of somatostatin are prepared. A single amino acid of D-configuration, functioning as a spacer for the remaining amino acids, replaces seven of the ring amino acids of somatostatin. The amino acid adjacent to this spacer amino acid is methylated on the nitrogen and is of the D-configuration. The two amino acids on either side of this dipeptide are also of D-configuration. The remaining two amino acids, Trp and Lys are either D- or L-. The order of the amino acids is reversed relative to the sequence found in somatostatin. The structures therefore represent a modified form of D-retro peptide analogs. The cyclic hexapeptides are easier to synthesize, have a longer duration of activity, and many have a greater level of activity than somatostatin. The compounds have the properties of inhibiting the release of glucagon, growth hormone and insulin. Certain of the compounds also are capable of inhibiting the release of gastric acid secretions. The compounds are particularly useful in the treatment of acromegaly, diabetes, diabetic retinopathy and peptic ulcers. These cyclic hexapeptides are prepared by the solid phase method.

10 Claims, No Drawings

MODIFIED D-RETRO CYCLIC HEXAPEPTIDE SOMATOSTATIN ANALOGS

BACKGROUND OF THE INVENTION

Somatostatin is a tetradecapeptide incorporating a cyclic dodecapeptide, having the structure:

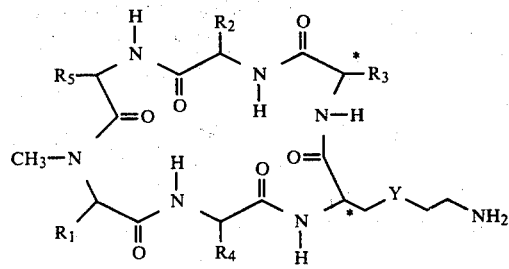

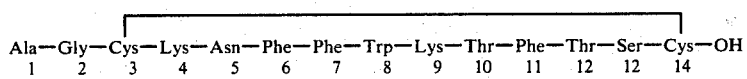

and has the properties of inhibiting the release of growth hormone, inhibiting the release of insulin and glucagon and reducing gastric secretion. Somatostatin itself has a short duration of action because it is inactivated, *inter alia,* by aminopeptidases and carboxypeptidases present *in vivo*. This problem of the short duration of action has been partially solved in the prior art by preparing derivatives of somatostatin which have low solubility, thus attaining a slow release on subcutaneous injection. Once dissolved, however, the derivatives are no more stable to inactivation by aminopeptidase and carboxypeptidases than somatostatin itself. Other attempted solutions to the instability of somatostatin have involved the preparation of smaller ring size and conformationally restricted analogs.

SUMMARY OF THE INVENTION

The present invention provides for cyclic hexapeptides which are derivatives of somatostatin in which, *inter alia,* seven of the ring amino acids are replaced by a single D-amino acid, both of the exo-cyclic amino acids are removed and the cyclic hexapeptide is in a modified form of the D-retro configuration. Further substitution and reaction of the remaining amino acids is also described. The cyclic hexapeptides inhibit the release of glucagon, growth hormone and insulin, and inhibit the release of gastric acid secretion. Specifically the compounds may preferentially inhibit the release of growth hormone without effecting the level of gastric secretion or without effecting the level of secretion of insulin and glucagon, or the compounds may inhibit the release of gastric acid secretion. Thus, the compounds have a more selective biological activity than somatostatin. The cyclic hexapeptide structure of the instant compounds also have a longer duration of activity than somatostatin. As such the instant cyclic hexapeptides are useful for the treatment of acromegaly, diabetes, diabetic retinopathy and peptic ulcers.

Thus, it is an object of the present invention to describe the D-retro cyclic hexapeptide somatostatin analogs. A further object is to describe procedures for the preparation of such D-retro cyclic hexapeptides. A still further object is to describe the use of such compounds in the treatment of acromegaly, diabetic retinopathy and peptic ulcers. Further objects will become apparent from reading the following description.

DESCRIPTION OF THE INVENTION

The compounds of the instant invention are best realized in the following structural formula:

wherein

Y is $(CH_2)_m$ wherein m is 0, 1 or 2 or sulfur such that the sulfur may be in any position along the chain;

$R_1$ and $R_2$ are independently loweralkyl, benzyl, substituted benzyl where the substituent may be one or two of loweralkyl, halogen, hydroxy, amino, nitro or loweralkoxy; and loweralkyl substituted with a 5- or 6-membered heterocyclic ring;

$R_3$ is 3-indolylmethyl or substituted 3-indolylmethyl wherein the substituent may be loweralkyl, loweralkoxy, or halogen;

$R_4$ is loweralkyl, hydroxyloweralkyl, benzyl, carboxyloweralkyl, aminoloweralkyl or substituted benzyl wherein the substituent may be loweralkyl, loweralkoxy, hydroxy, halogen, amino or nitro;

$R_5$ is hydrogen, loweralkyl, benzyl, or substituted benzyl wherein the substituent is loweralkyl, loweralkoxy, hydroxy, halogen, amino or nitro; and the two asymmetric centers marked with an asterisk (*) may be either D or L, provided the two centers of asymmetry are not the same, while the other asymmetric centers are D.

The term "loweralkyl" when used in the instant application is intended to represent those alkyl groups either straight or branched chain, which have from 1–5 carbon atoms. Examples of such alkyl groups are methyl, ethyl, propyl, iso-propyl, butyl, sec-butyl, pentyl and the like.

The term "loweralkoxy" is intended to include those alkoxy groups of from 1–5 carbon atoms, in either a straight or branched chain. Examples of such alkoxy groups are methoxy, ethoxy, propoxy, isopropoxy, butoxy, tert-butoxy, pentoxy and the like.

The term "halogen" or "halo" is intended to include fluorine, chlorine, bromine and iodine.

The term "5- or 6-membered heterocyclic ring" is intended to include those 5- or 6-membered heterocycles with 1- or 2-heteroatoms selected from oxygen, nitrogen and sulfur. Exemplary of such heterocycles is imidazole, furan, thiazole, pyrazole, pyridine and the like.

It will be appreciated by those skilled in the art that when $R_1$ and $R_2$ are benzyl, $R_3$ is indolylmethyl, Y is methylene, and $R_4$ is 1-hydroxyethyl, the 7,8,9,10 and 11 amino acids of somatostatin (-Phe-Trp-Lys-Thr-Phe-) are represented in D-retro form, with the somatostatin 11-position now containing a secondary amino acid, represented by N-methyl D-phenyl alanine and the somatostatin 6-position amino acid, represented by D-alanine when $R_5$ is methyl, has taken the place of the remainder of the somatostatin amino acids. Thus, using the above definitions of the substituent groups, the following representative cyclic hexapeptide analog of somatostatin is formed:

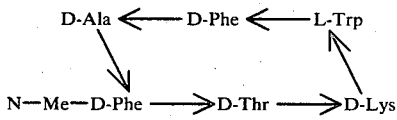

The perferred embodiments of the cyclic hexapeptides of this invention are realized in the foregoing structural formula wherein Y is $(CH_2)_n$ and n is 1;

$R_1$ and $R_2$ are as defined above;
$R_3$ is 3-indolylmethyl or substituted indolylmethyl wherein the substituent is methoxy or fluoro;
$R_4$ is methyl, ethyl, isopropyl, hydroxy methyl or hydroxyethyl, and
$R_5$ is methyl or ethyl.

Further preferred embodiments are realized when Y is methylene;
$R_1$ and $R_2$ are as defined above;
$R_3$ is 3-indolylmethyl;
$R_4$ is hydroxy ethyl or isopropyl; and
$R_5$ is methyl or ethyl.

The preferred $R_1$ and $R_2$ groups are loweralkyl, benzyl or substituted benzyl where the substituent is loweralkyl, halogen, hydroxy, amino, nitro or alkoxy.

Included within these preferred compounds are:
Cyclo-(D-Abu-N-Me-D-Phe-D-Val-L-Lys-D-Trp-D-Tyr)
Cyclo-(D-Ala-N-Me-D-Phe-D-Thr-L-Lys-D-Trp-D-Phe)
Cyclo-(D-Ala-N-Me-D-Phe-D-Val-L-Lys-D-Trp-D-Phe)
Cyclo-(D-Ala-N-me-D-Phe-D-Thc-D-Lys-L-Trp-D-Phe)

In the instant application several abbreviated designations are used for the amino acid components, certain preferred protecting groups, reagents and solvents. The meanings of such abbreviated designations are given in Table I.

TABLE I

| Abbreviated Designation | |
|---|---|
| | Amino Acid |
| Lys | lysine |
| Phe | phenylalanine |
| Trp | tryptophan |
| Thr | threonine |
| Aha | 7-aminoheptanoic acid |
| Tyr | tyrosine |
| Val | valine |
| Abu | α-aminobutyric acid |
| Ser | serine |
| Asn | asparagine |
| Pro | proline |
| Asu | amino-suberic acid |
| Cys | cysteine |
| | Protecting Groups |
| INOC | isonicotinyloxycarbonyl |
| BOC | tert-butyloxycarbonyl |
| OMe | methyl ester |
| Bu | tert-butyl |
| CBZ | benzyloxycarbonyl |
| Bzl | benzyl |

TABLE I-continued

| Abbreviated Designation | |
|---|---|
| 2-Cl-CBZ | 2-chlorobenzyloxycarbonyl |
| Acm | acetamidomethyl |
| Me | methyl |
| | Activating Groups |
| ONp | p-nitrophenyl ester |
| HSE | N—hydroxysuccinimide ester |
| HBT | 1-hydroxybenzotriazole |
| | Activating Agents |
| DCCI | dicyclohexylcarbodiimide |
| | Reagents |
| TFA | trifluoroacetic acid |
| TEA | triethylamine |
| DIPEA | diisopropylethylamine |
| EDT | ethanedithiol |
| | Solvents |
| EPAW | ethyl acetate-pyridine-acetic acid-water |
| BAW | butanol-acetic acid-water |
| CMW | chloroform-methanol-water |
| DMF | dimethylformamide |
| THF | tetrahydrofuran |

In accordance with the present invention, the novel D-retro cyclic hexapeptide somatostatin analogs are prepared by cyclizing corresponding linear peptides. The linear peptides are prepared by using the solid phase sequential synthesis technique. Accordingly, the process for preparing the cyclic hexapeptide somatostatin analogs of the present invention comprises (a) preparing a corresponding blocked linear peptide attached to a solid phase resin; (b) selectively deblocking the N-terminal amine group; (c) removing the linear peptide from the resin; (d) treating the linear peptide with a cyclizing agent to obtain the cyclic hexapeptide through the formation of an amide bond; (e) removing any side chain blocking groups.

When the linear peptide is prepared on the resin, it is generally not critical which amino acid is selected to be at the C-terminal position provided only that the sequence of amino acids in the linear peptide corresponds to that in the desired somatostatin analog. Once a linear peptide has been cyclized one can no longer determine which amino acid was at the C-terminus of the linear peptide.

While generally the selection of the first amino acid to start the chain is not critical, since the linear peptide will be cyclized, there may be other factors which may prefer one starting amino acid over another. For example Trp can react with t-butyl carbonium ions which are formed when BOC groups are removed. Thus, selection of a reaction sequence which places Trp at the N-terminal end of the linear peptide will cause Trp to be added last, and thus it will have the least exposure to t-butyl carbonium ions. This type of selection may not always be possible, such as where there are two indole containing moieties in the peptide. However, such reaction sensitivities should be considered when planning a peptide reaction sequence.

The synthesis of the linear peptides by the solid phase techinique is conducted in a stepwise manner on chloromethylated resin. The resin is composed of fine beads (20–70 microns in diameter) of a synthetic resin prepared by copolymerization of styrene with 1–2 percent divinylbenzene. The benzene rings in the resin are chloromethylated in a Friedel-Crafts reaction with chloromethyl methyl ether and stannic chloride. The Friedel-Crafts reaction is continued until the resin contains 0.5 to 5 mmoles of chlorine per gram of resin.

The amino acid selected to be the C-terminal amino acid or the linear peptide is converted to its amino protected derivative. The carboxyl group of the selected C-terminal amino acid is bound covalently to the insoluble polymeric resin support, as for example, as the carboxylic ester of the resin-bonded benzyl chloride present in chloromethyl-substituted polystyrene-divinylbenzene resin. After the amino protecting group is removed, the amino protected derivative of the next amino acid in the sequence is added along with a coupling agent, such as dicyclohexylcarbodiimide. The amino acid reactant may be employed in the form of a carboxyl-activated amino acid such as the ONp ester, an amino acid azide, and the like. Deprotection and addition of successive amino acids is performed until the desired linear peptide is formed.

The selection of protecting groups is, in part, dictated by particular coupling conditions, in part by the amino acid and peptide components involved in the reaction.

Amino-protecting groups ordinarily employed include those which are well known in the art, for example, urethane protecting substituents such as benzyloxycarbonyl (carbobenzoxy), p-methoxycarbobenzoxy, p-nitrocarbobenzoxy, t-butyloxycarbonyl, and the like. It is preferred to utilize t-butyloxycarbonyl (BOC) for protecting the a-amino group in the amino acids undergoing reaction at the carboxyl end of said amino acid. The BOC protecting group is readily removed following such coupling reaction and prior to the subsequent step by the relatively mild action of acids (i.e. trifluoro acetic acid, or hydrogen chloride in ethyl acetate).

The OH group of Thr and Ser can be protected by the Bzl group and the ε-amino group of Lys can be protected by the INOC group or the 2-chlorobenzyloxycarbonyl (2-CL-CBZ) group. In the case of Lys, it is preferred to protect the ε-amino group with 2-Cl-CBZ group as this group is removed simultaneously with the Bzl groups by treatment with HF after the linear peptide has been cyclized. The INOC group is not removed by HF and requires an additional treatment with Zn. Neither group is affected by TFA, used for removing BOC protecting groups. After the linear peptide is cyclized, the protective groups, such as 2-Cl-CBZ and Bzl, are removed by treatment with HF.

After the linear peptide has been formed on the solid phase resin, it may be removed from the resin by a variety of methods which are well known in the art. For example the peptide may be cleaved from the resin with hydrazine and thus directly form the peptide hydrazide which may be subsequently cyclized via the azide to the desired cyclic peptide. The hydrazide is converted to the corresponding azide by reaction with a reagent which furnishes nitrous acid *in situ*. Suitable reagents for this purpose include a lower alkyl nitrite (e.g. t-butyl nitrite, isoamyl nitrite) or an alkali metal nitrite salt (e.g., sodium nitrite, potassium nitrite) in the presence of a strong acid such as hydrochloric, phosphoric, etc. This reaction is carried out in the presence of either water and/or a non-aqueous solvent such as dimethylformamide, tetrahydrofuran, dioxane, chloroform, methylene chloride, etc., at a temperature between about −40° C. and +20° C. Alternatively, the peptide may be removed from the resin by treatment with a lower alcohol such as methanol in the presence of an organic base such as triethylamine, thus resulting in the formation of the corresponding lower alcohol ester of the linear peptide. The resulting ester may be converted to the hydrazide which may then be cyclized, via the azide, to the desired cyclic peptide. The preferred method for cleaving the peptide from the resin in the present invention is the use of hydrazine.

As reference Table II will show, one preferred overall procedure for preparing desired cyclic peptides of the present invention involves the stepwise synthesis of the linear peptide on a solid phase resin. More specifically, in the process for preparing:

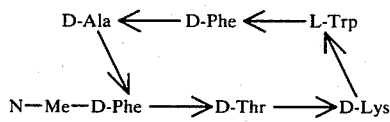

the carboxyl end of the $N^\alpha$-blocked amino acid $N^\alpha$-BOC-($N^\epsilon$-2-Cl-Cbz-D-lysine) is bound covalently to an insoluble polymeric resin support as the carboxylic acid ester of the resin-bonded benzyl chloride. The α-amino group of D-Lys is protected by the BOC group. After the attachment of the D-Lys is completed on the resin, the protecting group BOC is removed by treatment with TFA in $CH_2Cl_2$. The subsequent amino acids are attached, in the form of BOC-amino acid, using DCCI as the condensing agent or an active ester such as ONp. After the desired linear peptide has been prepared, the N-terminal amino group is selectively deblocked and the peptide is removed from the resin by treatment with hydrazine. The resulting linear peptide hydrazide with the N-terminal amino group deblocked having the amino acid sequence:

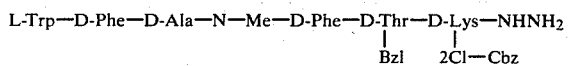

is treated with isoamyl nitrite in acid pH to form the corresponding azide. The azide solution is diluted with solvent and neutralized with an organic base. The linear peptide cyclizes to form:

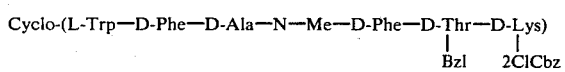

During the cyclization the "pH" is checked and maintained at neutral by the addition of organic base. The "pH" in organic solvent is determined by the application of an aliquot of the solution to moistened narrow range pH paper.

After the linear peptide is cyclized, the protective groups, 2-Cl-CBZ and OBzl, are removed by treatment with HF in the presence of anisole. The crude cyclic peptide obtained is purified chromatographically, preferably with column chromatography on silica gel. The elution solvent is generally an organic solvent or mixtures thereof which is selected by analyzing aliquots of the material using thin layer chromatography.

TABLE II

The reaction scheme for the preparation of one of the cyclic hexapeptides of this invention is outlined in the following series of reactions:

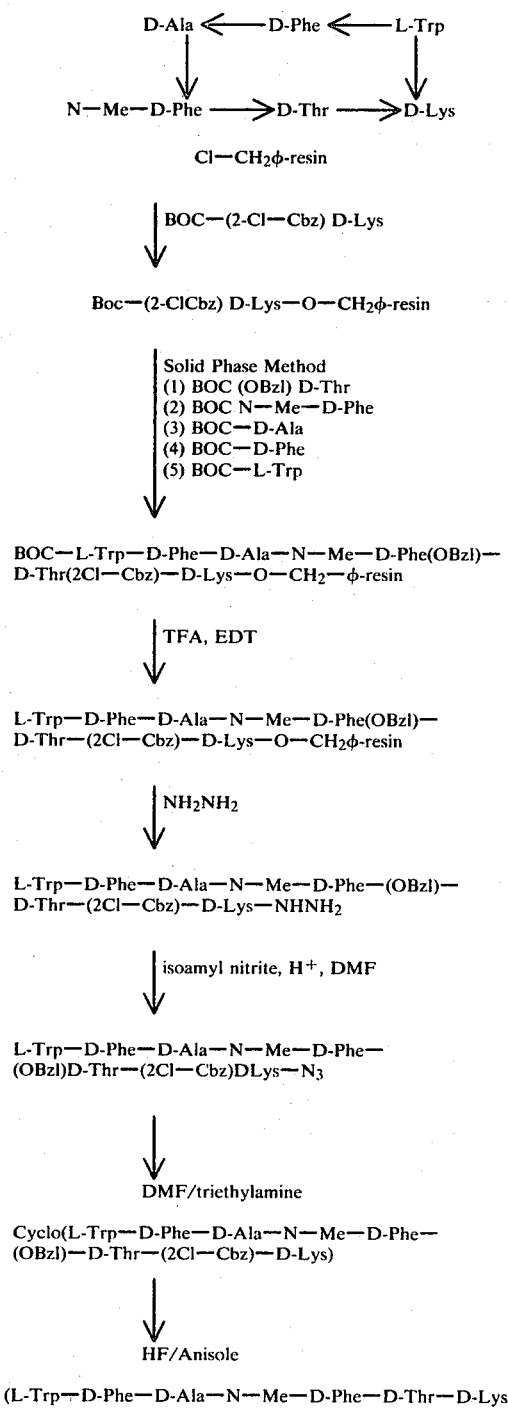

EXAMPLE 1

Preparation of L-Trp-D-Phe-D-Ala-N-Me-D-Phe-(OBzl)D-Thr-(2-Cl-Cbz)-D-Lys-OCH$_2\phi$-resin BOC-2-Cl-Cbz-D-Lys (8.28 g, 20 mmoles) and Cs$_2$CO$_3$ (3.25 g, 10 mmoles) were dissolved in a mixture of 12 ml of H$_2$O and 24 ml of EtOH. Solvents were removed *in vacuo*. The residue was evaporated to dryness *in vacuo* with DMF (2×40 ml). To the residue was added 80 ml of DMF and 25 g of 2% cross-linked Merrifield resin (0.96 mmoles chlorine/g). The reaction vessel was rotated on a rotary evaporator at 50° overnight. An additional 80 ml of DMF was added and the reaction was continued for 3 more hours. The resin was separated by filtration and washed with the following solvents:

2×250 ml of methanol-water (1:1)
2×250 ml of water
250 ml of DMF
250 ml of methanol
250 ml of DMF Fines were removed by suspending the resin in 250 ml of CH$_2$Cl$_2$ and draining CH$_2$Cl$_2$ after the resin rose to the top (4 times). The resin was washed with 2×250 ml of methanol and dried in vacuo overnight giving 30.35 g of Boc-(2-Cl-Cbz)-D-Lys-OCH$_2\phi$-resin containing 0.5 mmole of 2-Cl-Cbz-D-lysine/g of resin.

BOC-2-Cl-Cbz-D-Lys-O-CH$_2\phi$-resin (4.0 g.; 2.0 mmole) was carried through the procedures in Tables III and IV using 2 deblockings (2 minutes and 25 minutes) with 25% TFA in methylene chloride and 2.5 equivalents of BOC-amino acid in the required sequence until the desired BOC-hexapeptide-O-CH$_2\phi$-resin was obtained.

DCCI was used as the sole coupling agent in every step.

The coupling of each amino acid proceeded smoothly. Best yields were obtained when the coupling was repeated in each step. When the coupling was repeated, the initial two chloroform washes, the deblocking step and the succeeding three chloroform washes were all omitted and replaced by a single chloroform wash.

The coupling reactions were carried out in methylene chloride, freshly degassed DMF or a mixture of these two solvents. The N-terminal amino group was blocked with a BOC group in each case; the hydroxy group of Thr was blocked with Bzl and the ε-amino group of Lys with 2-Cl-CBZ.

When the desired BOC-hexapeptide-O-CH$_2$-$\phi$-resin was obtained, the N-terminal BOC group was removed by the terminal deblocking procedure set forth in Table V.

TABLE III

| Solvent or reagent (number of treatments | CHCl$_3$ (2) | 25% TFA in CH$_2$Cl$_2$ | CHCl$_3$(3) | NEt$_3$—CH$_2$CL$_2$ (1:9) | CHCl$_3$(3) CH$_2$Cl$_2$(3) | BOC AA in CH$_2$Cl$_2$ | 0.5M DCCI in CH$_2$Cl$_2$ | DMF(1) MeOH(1) DMF(1) |
|---|---|---|---|---|---|---|---|---|

TABLE III-continued

| or washes) | (2) | | (2) | | | (DMF or a mixture of both) | | MeOH(1) CHCl₃(2) |
|---|---|---|---|---|---|---|---|---|
| Vol. in ml. | 40 | 20 | 40 | 40 | 40 | 25 | 10 | 40 |
| Time in min. | 5 | 2 and 25 | 2 | 5 and 5 | 2 | 5 | 5 coupling 30 | 2 |

TABLE IV

| Protected Amino Acid | Solvent Ml. |
|---|---|
| BOC—(O—Bzl—D-Thr(1.55 g) Recouple | 25 ml. CH₂Cl₂ |
| BOC N—Me—D-Phe (1.40 g) Recouple | 25 ml. CH₂Cl₂ |
| BOC—D-Ala (0.95 g) Recouple | 25 ml. CH₂Cl₂ |
| BOC—D-Phe (1.32 g) Recouple | 25 ml. CH₂Cl₂ |
| BOC—L-Trp (1.52 g) Recouple | 15 ml. CH₂Cl₂, 5 ml. DMF |

TABLE V

TERMINAL DEBLOCKING PROGRAM

| Solvent or reagent (number or treatments or washes) | CHCl₃(1) | 25% TFA in CH₂Cl₂ + 1% Ethanedithiol (2) | CHCL₃ (3) | MeOH(2) CH₂Cl₂ MeOH(2) CH₂Cl₂(2) |
|---|---|---|---|---|
| Vol. in ml. | 40 | 40 | 40 | 40 |
| Time in minutes | 5 | 2 and 25 | 2 | 2 |

After the procedures of Tables III, IV, and V were completed, the blocked hexapeptide-OCH₂-φ-resin is dried overnight and weighs 5.33 g.

EXAMPLE 2

Preparation of
L-Trp-D-Phe-D-Ala-N-Me-D-Phe-(OBzl-D-Thr-(2Cl-Cbz)-DLys-NHNH2

All of the resin from Example 1 is combined with 50 ml. of a 1:1 mixture of methanol and hydrazine and stirred at room temperature for 1 hour. The insoluble resin is removed by filtration and the solution is evaporated to remove the methanol and hydrazine. The residue is placed under high vacuum overnight to remove all volatile materials. The residue is triturated with water, filtered and dried over P₂O₅ in vacuo affording 1.636 g. which is used as is in the next step.

EXAMPLE 3

Preparation of
L-Trp-D-Phe-D-Ala-N-Me-D-Phe-(OBzl)-D-Thr-(2-Cl-Cbz)-D-Lys-N₃

The dried material from Example 2 is combined with 15 ml. of degassed dimethylformamide under a blanket of nitrogen and cooled to −15° C., and 5 equivalents of 5.32 N. hydrogen chloride in tetrahydrofuran (1.4 ml.) is added. The solution is cooled to −25° C. and 5 ml. of a 1:1: mixture of isoamyl nitrite in dimethylformamide is added in portions until a positive starch/KI test is obtained. The completion of the reaction is followed by thin layer chromatography and the disappearance of the hydrazide starting material.

EXAMPLE 4

Preparation of Cyclo
(L-Trp-D-Phe-D-Ala-N-Me-D-Phe-(OBzl)
D-Thr-(2Cl-Cbz)D-Lys

The azide compound of Example 3 without isolation is added to 700 ml. of degassed dimethylformamide, precooled to −50° C., the pH adjusted to 8, with triethylamine, and the reaction mixture placed in the freezer for 24 hours. The pH is readjusted to 8 if necessary after about 14 hours and the mixture is stored for 16 hours at 5° C. Thin layer chromatography indicates that the reaction is completed. The mixture is concentrated to dryness, dissolved in 150 ml. of a 3:1 dimethyl-formamide/water mixture and treated with a mixed bed anion-cation exchange resin for 1 hour. The mixture is filtered and concentrated to dryness in vacuo to an oil, and the residue is dissolved in 3 ml. of ethyl acetate and 32 ml. of ether is slowly added causing a precipitate. The liquid is decanted and the residue triturated with petroleum ether affording a solid which is washed with ether-petroleum-ether (1:1) and dried affording 1.36 g. of cyclic hexapeptide.

EXAMPLE 5

Preparation of Cyclo (L-Trp-D-Phe-D-Ala-N-Me D-Phe-D-Thr-D-Lys)

1.36 g. of the protected cyclic hexapeptide of Example 4 is combined in a teflon lined chamber with 2 ml. of anisole. The chamber is then evacuated and filled to a total volume of 30 ml. with liquid hydrogen fluoride at the temperature of the dry ice/acetone bath. The temperature is raised to 0° C. and stirring continued for 1 hour. The hydrogen fluoride is allowed to evaporate and residue placed in vacuo until a slurry is formed. The slurry is triturated with ethyl acetate and a gummy precipitate formed. The gum is triturated with 25 ml. of ether, and 50 ml. of petroleum ether added affording 1.09 g. of solid. The powder is placed on 400 g. of silica gel and eluted with 22 ml. fractions of chloroform-methanol-concentrated ammonium hydroxide (80-20-2) Fractions 40–60 are combined and concentrated affording 300 mg of product.

Following the above procedure, and by modifying only the selection and order of amino acids in the process of Example 1, there are prepared other cyclic hexapeptides of this invention.

The instant cyclic hexapeptide analogs ofsomatostatin are tested and compared with the effects of somatostatin in an in vitro test for the inhibition of growth hormone. The test is described as follows:

"Rat pituitaries" were isolated according to the procedures of Vale and Grant 'In vitro Pituitary Hormone Secretion Assay for Hypophysiopic Substances' in Methods in Enzymology. Vol.XXXVII, eds. O'Malley, B. W. and Hardman, J. G. (Academic Press, Inc., New York) pp.5–93 (1975).

"After 4 days in culture, the cells were washed and incubated for 4 hours in Dulbecco-modified Eagle's medium in the presence or absence of graded doses of each analog of somatostatin. The medium was then collected for subsequent growth hormone determination by a double antibody radioimmunoassay for rat growth hormone."

The test results for some of the compounds of this invention are recorded below with the results for somatostatin listed first and given the arbitrary value of 1. The results for the instant compounds are given as multiples or fractions of the effect of somatostatin. The first of the instant compounds listed is the compound prepared in Examples 1-5. The compound is written slightly different, however, to conform to the order of the amino acids found in somatostatin.

Activity of Cyclichexapeptide Analogs of Somatostatin

| Compound | Growth Hormone Release Inhibition In Vitro |
|---|---|
| Somatostatin | 1 |
| Cyclo-(D-Ala—N—Me—D-Phe—D-Thr—D-Lys—L-Trp—D-Phe) | 0.27 |
| Cyclo-(D-Ala—N—Me—D-Phe—D-Val—L-Lys—D-Trp—D-Phe) | 0.3 |
| Cyclo-(D-Abu—N—Me—D-Phe—D-Val—L-Lys—D-Trp—D-Tyr) | 2.4 |
| Cyclo-(D-Ala—N—Me—D-Phe—D-Thr—L-Lys—D-Trp—D-Phe) | 0.88 |

The gastric effects of the instant cyclichexapeptide analogs of somatostatin are determined by the following procedure.

Compounds are tested for their ability to inhibit pentagastrin evoked gastric secretion in the chronic fistula dog. Female beagle dogs with a chronic gastric fistula are given pentagastrin (2.5 ug./kg./hour,i.v. from −60 to 120 min. and gastric outputs are collected via the fistula cannula. Samples are analyzed at 30 minute intervals for volume (ml.) and titratable acid (mEq/L) (Titration to pH 7 with 0.01 N NaOH); total acid output (mEq) is calculated as the production of output volume and acid concentration. Test compounds are infused at a constant rate from 0 to 60 minutes. Data are generally expressed as percent change of total acid output relative to a placebo trial in the same animals.

What is claimed:
1. A compound having the formula:

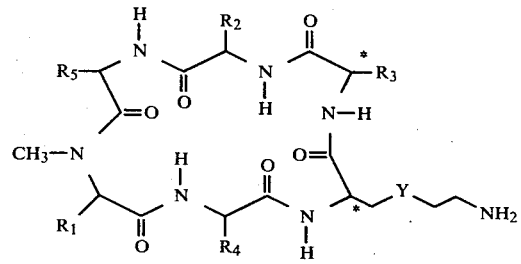

wherein
Y is $(CH_2)_m$ wherein m is 0, 1 or 2 or sulfur such that the sulfur may be in any position along the chain;
$R_1$ and $R_2$ are independently lower alkyl, benzyl, substituted benzyl wherein the substituent may be one or two of loweralkyl, halogen, hydroxy, amino, nitro or loweralkoxy; and loweralkyl substituted with a 5- or 6-membered heterocyclic ring;
$R_3$ is 3-indolylmethyl or substituted 3-indolylmethyl wherein the substituent may be loweralkyl, loweralkoxy or halogen;
$R_4$ is loweralkyl, hydroxyloweralkyl, benzyl, carboxyloweralkyl, aminoloweralkyl or substituted hyroxy benzyl wherein the substituent may be loweralkyl, loweralkoxy, hydroxy, halogen, amino or nitro;
$R_5$ is hydrogen, loweralkyl, benzyl, or substituted benzyl wherein the substituent is loweralkyl, loweralkoxy, hydroxy, halogen, amino ornitro; and the two asymmetric centers marked with an asterisk (*) may be either D or L provided the two centers of asymmetry are not the same, while the other asymmetric centers are D.

2. A compound of claim 1 wherein Y is $(CH_2)n$ and n is 1;
$R_1$ and $R_2$ are as defined in claim 1;
$R_3$ is 3-indolylmethyl or substituted indolylmethyl wherein the substituent is methoxy or fluoro;
$R_4$ is methyl, ethyl, isopropyl, hydroxymethyl or hydroxyethyl; and
$R_5$ is as defined in claim 1.

3. A compound of claim 2 wherein $R_5$ is methyl or ethyl.

4. A compound of claim 3 wherein:
Y is methylene;
$R_1$ and $R_2$ are as defined in claim 1.
$R_3$ is 3-indolylmethyl;
$R_4$ is hydroxyethyl; and
$R_5$ is methyl.

5. The compound of claim 2 which is cyclo (D-Ala-N-Me-D-Phe-D-Thr-D-Lys-L-Trp-D-Phe).

6. The compound of claim 2 which is cyclo (D-Ala-N-Me-D-Phe-D-Val-L-Lys-D-Trp-D-Phe).

7. The compound of claim 2 which is Cyclo-(D-Ala-N-Me-D-Phe-D-Thr-L-Lys-D-Trp-D-Phe).

8. The compound of claim 2 which is cyclo-(D-Abu-N-Me-D-Phe-D-Val-L-Lys-D-Trp-D-Tyr).

9. A method for the treatment of acromegaly, diabetes, diabetic retinopathy and gastric ulcers which comprises administering to an animal requiring such treatment an effective amount of a D-retro cyclic hexapeptide of claim 1.

10. A pharmaceutical composition useful for the treatment of acromegaly, diabetes, diabetic retinopathy and gastric ulcers comprising a therapeutically effective amount of the D-retro cyclic hexapeptide of claim 1 or the non-toxic acid addition salts thereof in a pharmaceutically acceptable liquid or solid carrier.

* * * * *